(12) United States Patent
Geller et al.

(10) Patent No.: US 7,674,917 B2
(45) Date of Patent: Mar. 9, 2010

(54) PROCESS FOR PREPARING SUBSTITUTED THIOPHENESULFONYL ISOCYANATES

(75) Inventors: Thomas Geller, Odenthal (DE); Jörn Stölting, Cologne (DE)

(73) Assignee: Bayer CropScience AG, Monheim (DE)

( * ) Notice: Subject to any disclaimer, the term of this patent is extended or adjusted under 35 U.S.C. 154(b) by 427 days.

(21) Appl. No.: 11/722,509

(22) PCT Filed: Dec. 14, 2005

(86) PCT No.: PCT/EP2005/013407

§ 371 (c)(1),
(2), (4) Date: Jun. 21, 2007

(87) PCT Pub. No.: WO2006/072376

PCT Pub. Date: Jul. 13, 2006

(65) Prior Publication Data

US 2009/0281334 A1    Nov. 12, 2009

(30) Foreign Application Priority Data

Dec. 29, 2004    (DE) .................. 10 2004 063 192

(51) Int. Cl.
*C07D 333/34*    (2006.01)
(52) U.S. Cl. ........................................ 549/64
(58) Field of Classification Search ............ 549/64
See application file for complete search history.

(56) References Cited

U.S. PATENT DOCUMENTS 4,481,029 A    11/1984    Levitt

FOREIGN PATENT DOCUMENTS

EP    0030 142    6/1981
WO    WO 01/05788    1/2001
WO    WO 01/10863    2/2001

*Primary Examiner*—Taofiq A Solola
(74) *Attorney, Agent, or Firm*—Baker Donelson Bearman Caldwell & Berkowitz, P.C.

(57) ABSTRACT

The present invention relates to a process for preparing compounds of the general formula (I)

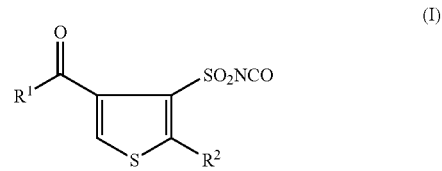

in which $R^1$ and $R^2$ are as defined in the description
by reacting compounds of the formula (II)

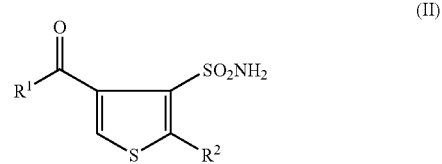

in which $R^1$ and $R^2$ are as defined in the description
with phosgene in the absence of a base and in the presence of one or more diluents and also optionally of a catalyst.

8 Claims, No Drawings

PROCESS FOR PREPARING SUBSTITUTED THIOPHENESULFONYL ISOCYANATES

CROSS REFEREMCE TO RELATED APPLICATIONS

This is a §371 National Stage Application of International Application No. PCT/EP2005/013407 filed Dec. 14, 2005, which claims priority from German Application No. 10 2004 063 192.1 filed Dec. 29, 2004.

BACKGROUND OF THE INVENTION 1. Field of the Invention

The invention relates to a novel process for preparing 2,4-disubstituted thiophene-3-sulfonyl isocyanates which are described as intermediates for active ingredients in agriculture, especially for substituted herbicidally active thienylaminocarbonyltriazolinones (cf. WO 01/05788) and sulfonylureas (WO 01/10863). 2. Description of Related Art It is known that certain substituted thienylsulfonyl isocyanates can be prepared by phosgenation in the presence of organic bases, in particular the base DABCO, from the corresponding sulfonamides (EP-A 30 142, U.S. Pat. No. 4,481,029). However, a disadvantage of this process is that an expensive organic base has to be used.

SUMMARY OF THE INVENTION

It has now been found in accordance with the invention that the preparation of the specific substituted 2-alkyl-4-alkoxycarbonyl-disubstituted thiophene-3-sulfonyl isocyanates can likewise be carried out in high yield without significant formation of by-products without adding the customary bases.

It has accordingly been found that compounds of the formula (I)

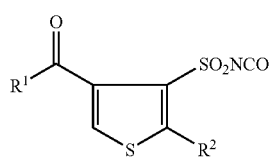

(I)

in which
$R^1$ is alkoxy having from 1 to 4 carbon atoms, and
$R^2$ is alkyl having from 1 to 4 carbon atoms, are obtained in very good yields and in high purity when compounds of the formula (II)

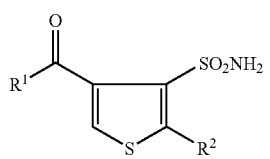

(II)

in which $R^1$ and $R^2$ are as defined above are reacted with phosgene in the absence of a base and in the presence of one or more diluents and also optionally of a catalyst.

DETAILED DESCRITION OF A PREFERRED EMBODIMENT

In the formula (I), $R^1$ is preferably methoxy, ethoxy, n- or i-propoxy. $R^2$ is preferably methyl, ethyl, n- or i-propyl. $R^1$ is more preferably methoxy. $R^2$ is more preferably methyl.

By virtue of the reaction of the sulfonamides without use of an organic base, a new process has surprisingly been found which allows the preparation of the 2,4-disubstituted thienyl-3-sulfonyl isocyanates in very good yields and in high purity with a short reaction time.

The process according to the invention thus constitutes an enrichment of the prior art since it allows a very advantageous preparation of 2,4-disubstituted thienyl-3-sulfonyl isocyanates. The access to the herbicidal thienylaminocarbonyltriazolinones and sulfonylureas based on these intermediates is thus eased.

The compounds of the formula (II) are known and can be prepared as specified in WO 01/05788 or by processes known in principle (cf., for example, EP-A 30 412, U.S. Pat. No. 4,481,029).

In the inventive reaction of the substituted sulfonamides with phosgene, operation is effected generally at temperatures between 20° C. and 170° C., preferably between 100° C. and 150° C., more preferably between 125° C. and 135° C. The diluents used in the reaction are preferably optionally halogenated aromatic hydrocarbons, for example chlorobenzene, toluene or xylene. Xylene and chlorobenzene are particularly preferred as diluents.

In the inventive reaction of the sulfonamides with phosgene, the reaction times are generally between 30 minutes and 6 hours, preferably between 2 and 4 hours.

To carry out the process according to the invention, the compounds of the formula (I) are prepared preferably by using the reagent in an equimolar amount or in excess. In general, between 1.0 and 10 mol, preferably between 1.0 and 3 mol, of phosgene are used per mole of sulfonamide of the formula (II). However, greater excesses of phosgene may also be used in accordance with the invention.

The process according to the invention is carried out generally under standard pressure. However, it is also possible to carry out the process according to the invention under elevated or reduced pressure, generally between 0.1 bar and 10 bar.

The process according to the invention should advantageously be carried out in the presence of a catalyst. The catalyst used may be a catalytically active amount of a butyl isocyanate or pentyl isocyanate. The preferred concentration of this isocyanate in the reaction is from 0.1 to 5 mol per mole of sulfonamide, preferably from 0.7 to 1.3 mol.

By their nature, the substituted sulfonamides can also be reacted with the isocyanate used as a catalyst to give the corresponding ureas. These can then be reacted in a second step with phosgene likewise to give the corresponding isocyanates.

The compounds of the formula (I) obtained by the process according to the invention may be isolated before they are used to prepare herbicidal end products. However, it is also possible to react the resulting compounds further directly without intermediate isolation. It is even preferred to prepare herbicidal thienylsulfonylaminocarbonyltriazolinones by reacting the resulting compounds of the formula (I) directly with the amines (for example the triazolinones).

The present invention therefore also provides a process in which the compounds of the formula (I) are reacted with a triazolinone in a subsequent reaction step without intermediate isolation ("one-pot process", cf. preparation example 3).

PREPARATION EXAMPLES

Example 1

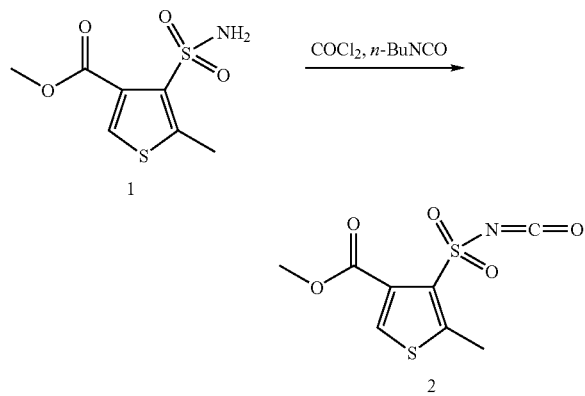

23.5 g of methyl 4-(aminosulfonyl)-5-methylthiophene-3-carboxylate (1) (100 mmol) were initially charged in 250 ml of xylene. From this mixture, approx. 70 ml of xylene were distilled off on a water separator. After addition of 9.9 g of n-butyl isocyanate (100 mmol), the reaction mixture was heated to reflux. Subsequently, 24 g of phosgene were introduced over a period of 3 h at such a rate that the temperature remained at approx. 130° C. (excess phosgene was kept in the system by a phosgene condenser). For workup, the mixture was cooled to room temperature and excess phosgene was removed by passing an argon stream through. Subsequently, distillative purification was effected, in which the butyl isocyanate can be recovered. The methyl 4-(isocyanatosulfonyl)-5-methylthiophene-3-carboxylate (2) can then be recovered as a colorless solid after a distillation under reduced pressure. 22 g of the methyl 4-(isocyanatosulfonyl)-5-methylthiophene-3-carboxylate (2) were obtained (83% of theory, content: 98%, b.p.: 120° C., 0.4 mbar). The identification and the determination of content were conducted by means of derivatization with methanol to the corresponding carbamate ($^1$H NMR (400 MHz, d$^6$DMSO): 2.72 (s), 3.61 (s), 3.79 (s), 8.00 (s), 11.96 (s)).

Example 2

Under the conditions specified above, 23.5 g of methyl 4-(aminosulfonyl)-5-methylthiophene -3-carboxylate (1) were reacted with 11.3 g of pentyl isocyanate (100 mmol) in the presence of phosgene to give methyl 4-(isocyanatosulfonyl)-5-methylthiophene-3-carboxylate (2). 22 g of this isocyanate (83% of theory, content: 99%, b.p.: 120° C., 0.4 mbar) were likewise obtained. The identification and the determination of content were conducted by means of derivatization with methanol to the corresponding carbamate ($^1$H NMR (400 MHz, d$^6$DMSO): 2.72 (s), 3.61 (s), 3.79 (s), 8.00 (s), 11.96 (s)).

Example 3

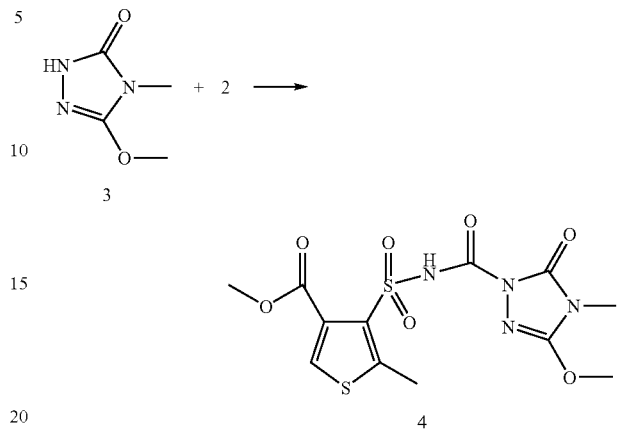

12.9 g of 5-methoxy-4-methyl-2,4-dihydro-3H-1,2,4-triazol-3-one (3) (100 mmol) were initially charged in 200 ml of xylene and heated to 70° C. At this temperature, 119 g of a 22% solution of methyl 4-(isocyanatosulfonyl)-5-methylthiophene-3-carboxylate (2) (100 mmol) in dry xylene were metered in. The mixture was stirred at 70° C. for a further 5.8 h. Subsequently, workup was effected at room temperature by filtering the precipitated product. After washing with 50 ml of xylene and subsequently drying, 36.4 g of methyl 4-({[(3-methoxy-4-methyl-5-oxo-4,5-dihydro-1H-1,2,4-triazol-1-yl)carbonyl]amino}-sulfonyl)-5-methylthiophene-3-carboxylate (4) (91% of theory, content relative to standard: 97.5%) of melting point 201° C. were obtained.

Alternatively to the two-step procedure (separate preparation of the isocyanate and subsequent reaction with the amine), it is possible, after the phosgene has been removed (isocyanate preparation) and the isocyanate used as a catalyst has been distilled off, to react the xylenic solution obtained from the preparation of methyl 4-(isocyanatosulfonyl) -5-methylthiophene-3-carboxylate (2) directly with the amine ("one-pot process"). Removal of the isocyanate used as a catalyst is not absolutely necessary for the success of the reaction with the amine.

What is claimed is:

1. A process for preparing a compound of formula (I)

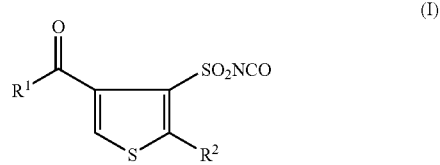

in which
R$^1$ is alkoxy having from 1 to 4 carbon atoms, and
R$^2$ is alkyl having from 1 to 4 carbon atoms, comprising reacting a compound of formula II

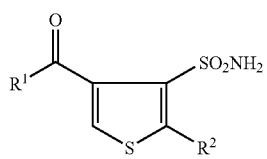

(II)

with phosgene in the absence of a base and in the presence of at least one diluent and also optionally of a catalyst.

2. The process as claimed in claim 1, wherein the reaction is carried out at a temperature from 100° C. to 150° C.

3. The process as claimed in claim 1, wherein the diluent is selected from the group consisting of chlorobenzene and xylene.

4. The process as claimed in claim 1, wherein the compound of formula (I) is reacted with an amine in a subsequent reaction step without intermediate isolation.

5. The process as claimed in claim 4, wherein the amine is 5-methoxy -4-methyl-2,4-dihydro-3H-1,2,4-triazol-3-one.

6. The process as claimed in claim 1, which is performed in the presence of a catalytically active amount of a butyl isocyanate or pentyl isocyanate.

7. A process of claim 1, wherein from 1.0-10 mol of phosgene is used per mole of the compound of formula II.

8. A process of claim 2, wherein from 1.0-10 mol of phosgene is used per mole of the compound of formula II.

* * * * *